United States Patent
Navia et al.

(10) Patent No.: US 7,473,237 B2
(45) Date of Patent: Jan. 6, 2009

(54) APPARATUS FOR AUTO-RETROPERFUSION OF A CORONARY VEIN

(75) Inventors: Jose L. Navia, Shaker Heights, OH (US); Jose Antonio Navia, Buenos Aires (AR); Jorge Luis Jordana, Buenos Aires (AR); Ji-Feng Chen, Lakewood, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 247 days.

(21) Appl. No.: 11/325,816

(22) Filed: Jan. 5, 2006

(65) Prior Publication Data

US 2006/0195060 A1 Aug. 31, 2006

Related U.S. Application Data

(63) Continuation-in-part of application No. 10/786,788, filed on Feb. 25, 2004, now Pat. No. 7,004,925.

(60) Provisional application No. 60/449,883, filed on Feb. 25, 2003.

(51) Int. Cl.
*A61M 37/00* (2006.01)
*A61M 29/00* (2006.01)

(52) U.S. Cl. ............ 604/6.13; 604/6.16; 604/4.01; 604/96.01; 604/103.05

(58) Field of Classification Search ............ 604/4.01, 604/6.14, 6.16, 6.11, 6.13, 96.01, 8–10, 75.01, 604/19, 27–29, 500, 506–510, 93.01, 104, 604/97.01, 523, 524, 533–535, 103.05, 103.09, 604/105–107, 907, 915, 99.04; 422/44, 45; 600/433–435; 623/1.11, 1.12
See application file for complete search history.

(56) References Cited

U.S. PATENT DOCUMENTS

| 3,331,371 | A | * | 7/1967 | Rocchi et al. | 604/99.04 |
|---|---|---|---|---|---|
| 4,459,977 | A | * | 7/1984 | Pizon et al. | 600/17 |
| 4,705,507 | A | * | 11/1987 | Boyles | 604/99.04 |
| 5,224,938 | A | * | 7/1993 | Fenton, Jr. | 604/247 |
| 5,324,260 | A | | 6/1994 | O'Neill et al. | |
| 5,597,377 | A | | 1/1997 | Aldea | |
| 5,755,687 | A | * | 5/1998 | Donlon | 604/508 |
| 5,824,071 | A | | 10/1998 | Nelson et al. | |
| 5,938,582 | A | | 8/1999 | Ciamacco, Jr. et al. | |
| 6,186,972 | B1 | | 2/2001 | Nelson et al. | |
| 6,340,356 | B1 | * | 1/2002 | Navia et al. | 604/104 |
| 6,447,539 | B1 | | 9/2002 | Nelson et al. | |
| 6,500,145 | B1 | | 12/2002 | Bicakci et al. | |
| 6,562,066 | B1 | | 5/2003 | Martin | |

(Continued)

FOREIGN PATENT DOCUMENTS

EP 0 249 338 A2 12/1987

*Primary Examiner*—Leslie R Deak
(74) *Attorney, Agent, or Firm*—Tarolli, Sundheim, Covell & Tummino LLP

(57) ABSTRACT

An apparatus and method for automatically retroperfusing a coronary vein. The apparatus includes an intraluminal graft having a tubular body extending between a proximal end and a distal end. The proximal end is for fluidly connecting to an artery to automatically supply retrograde blood for retroperfusion. The tubular body and the distal end are extendable into a vein that is fluidly connected with the coronary vein to be retroperfused. The distal end includes an expandable stent for securing the distal end in the coronary vein.

2 Claims, 12 Drawing Sheets

U.S. PATENT DOCUMENTS

| | | | |
|---|---|---|---|
| 7,004,925 B2 * | 2/2006 | Navia et al. ................ | 604/6.14 |
| 7,004,926 B2 * | 2/2006 | Navia et al. ................ | 604/6.14 |
| 2001/0027287 A1 | 10/2001 | Shmulewitz et al. | |
| 2002/0091354 A1 | 7/2002 | Navia et al. | |
| 2003/0181843 A1 | 9/2003 | Bibber et al. | |
| 2005/0101902 A1 | 5/2005 | Navia et al. | |

* cited by examiner

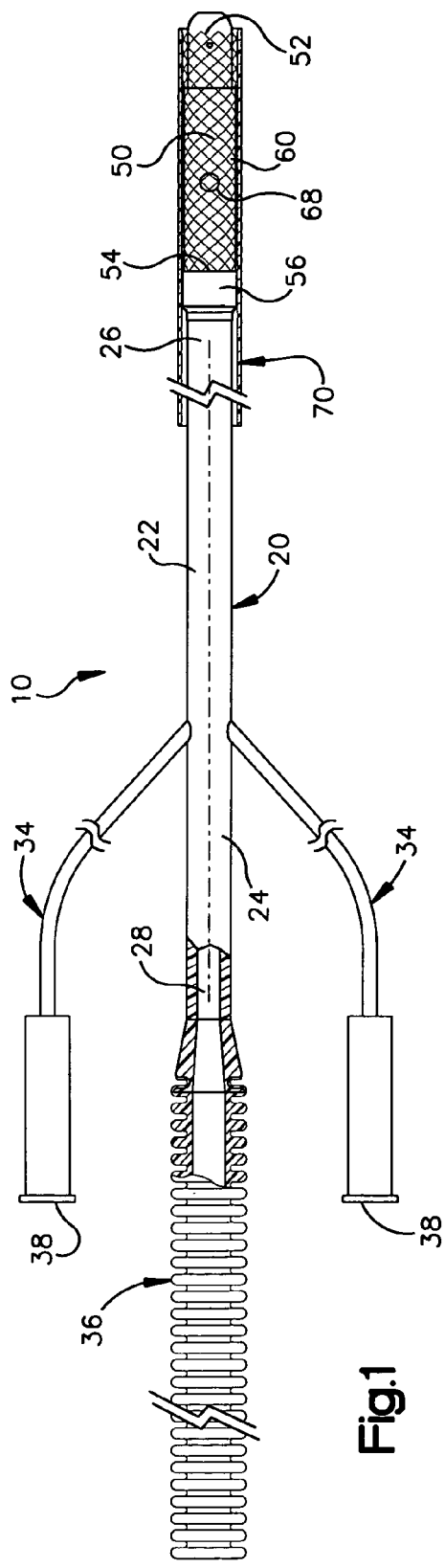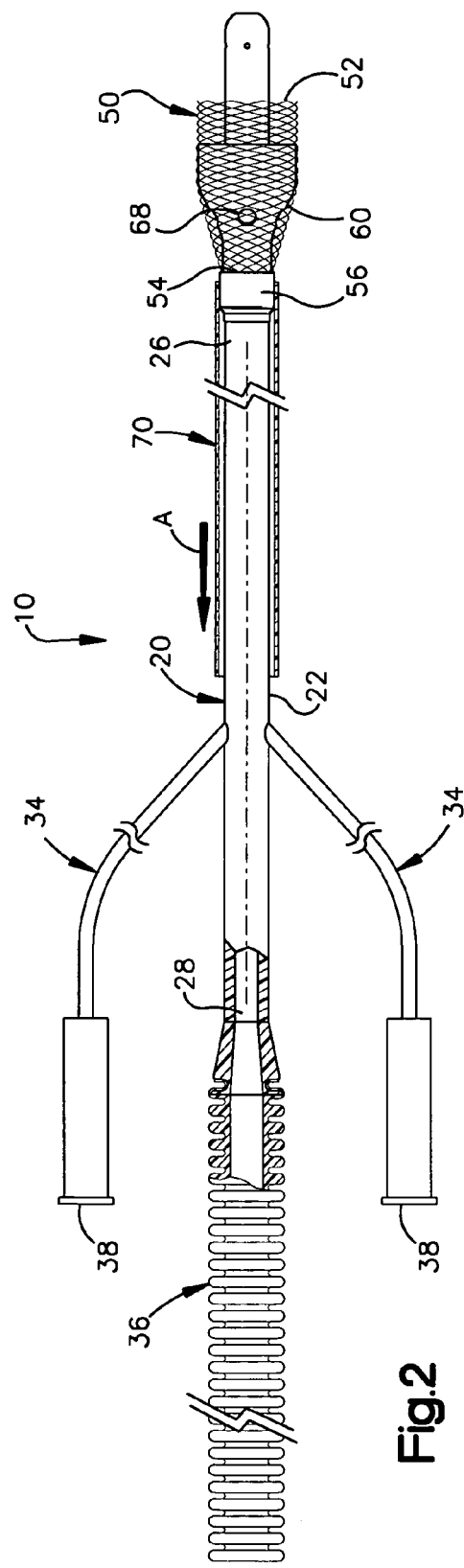

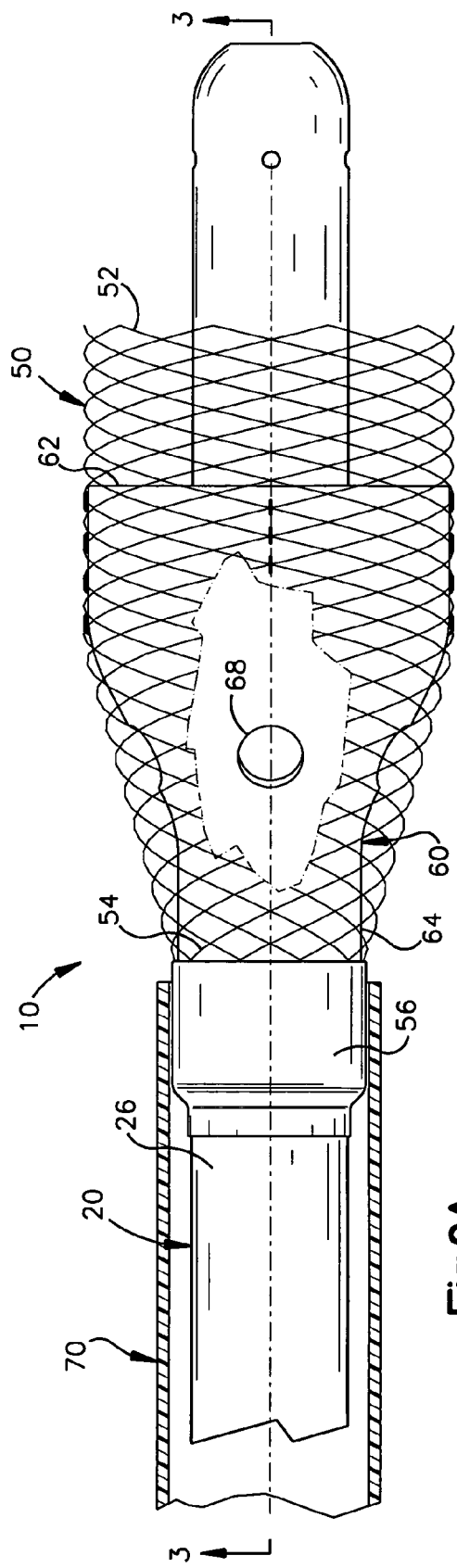
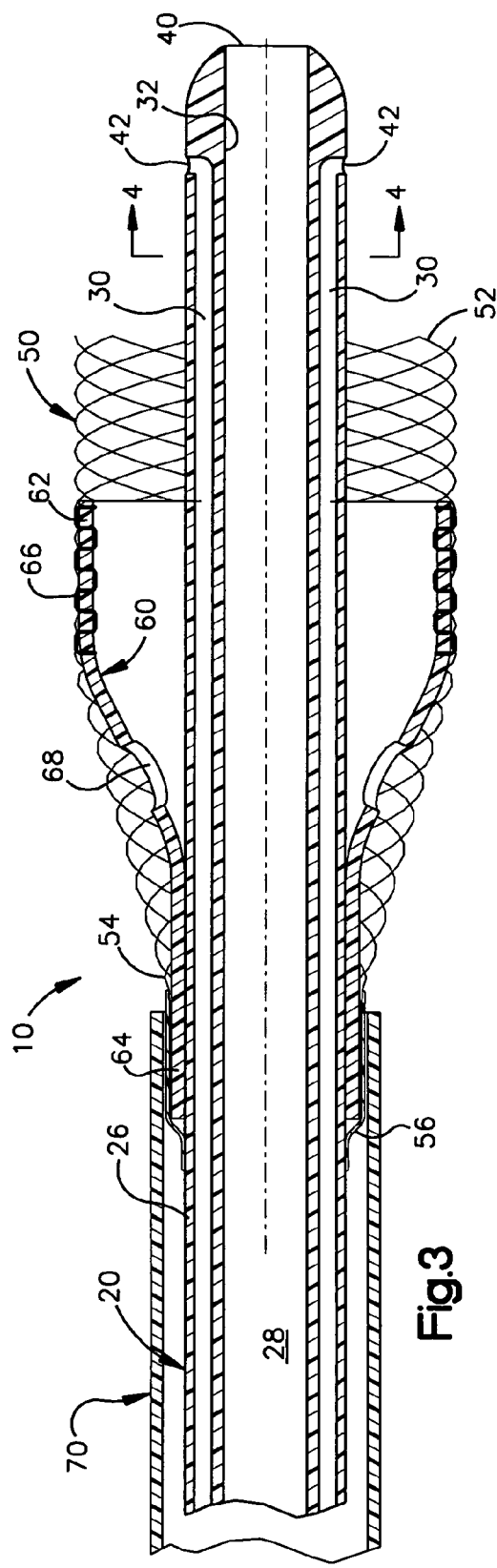
Fig.2A
Fig.3

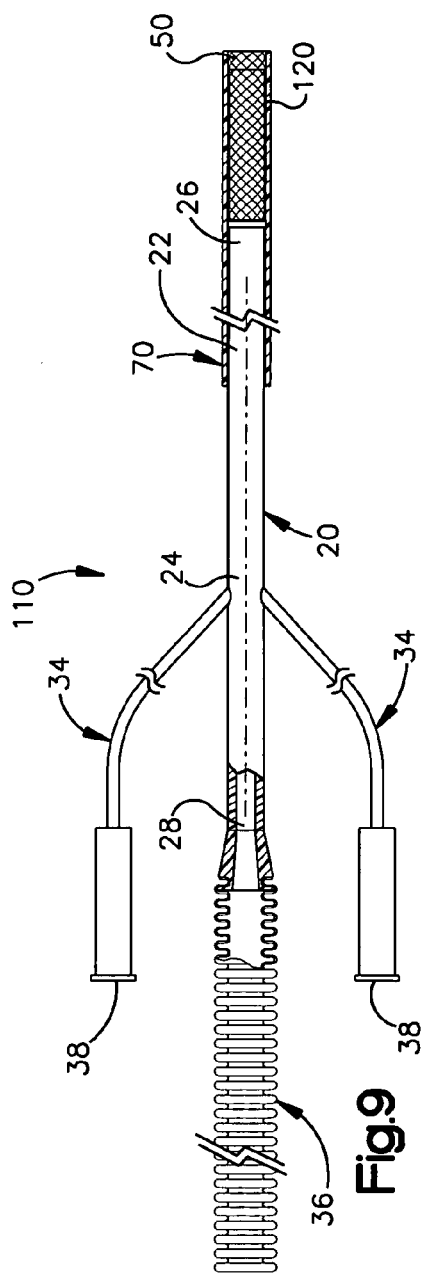
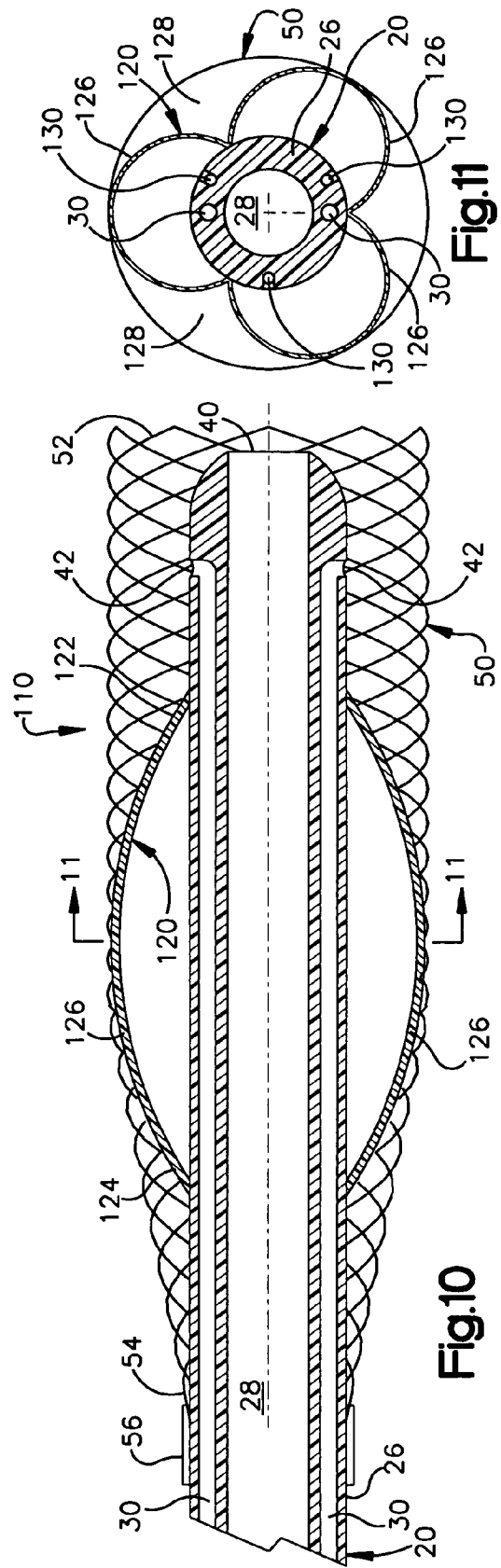

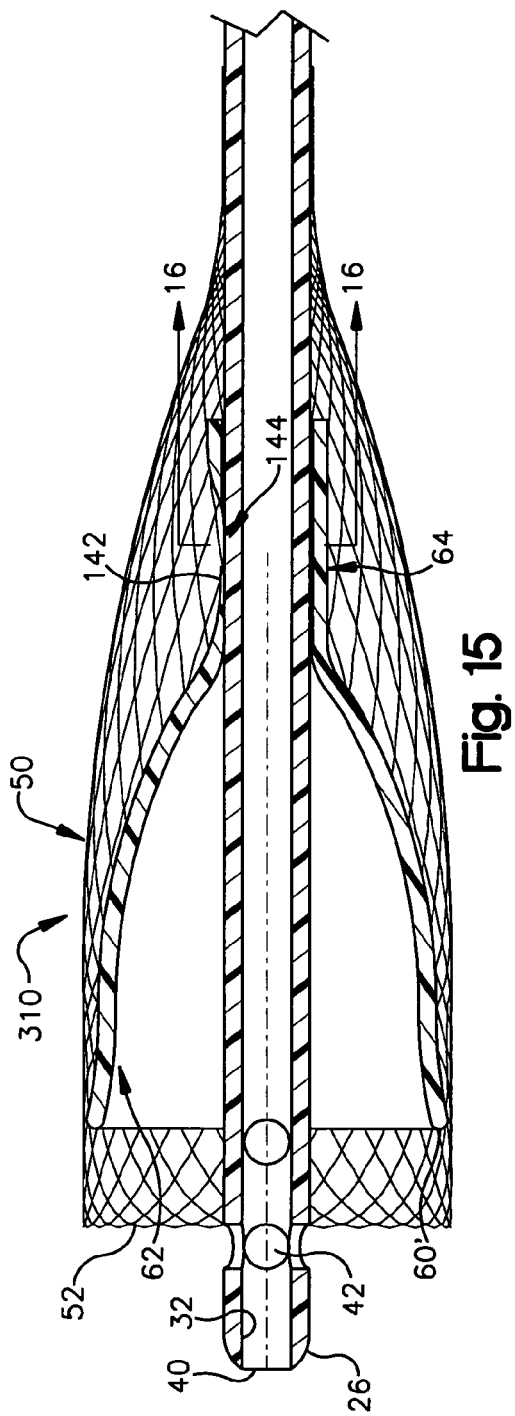
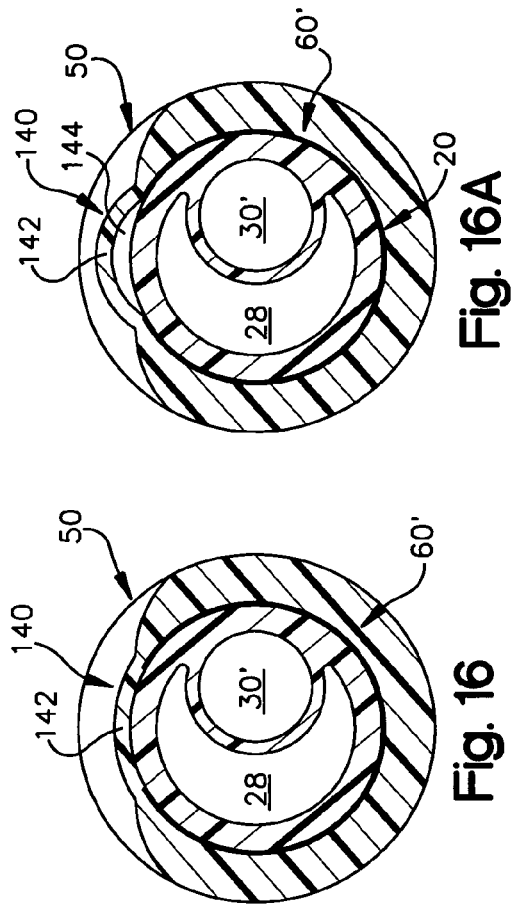
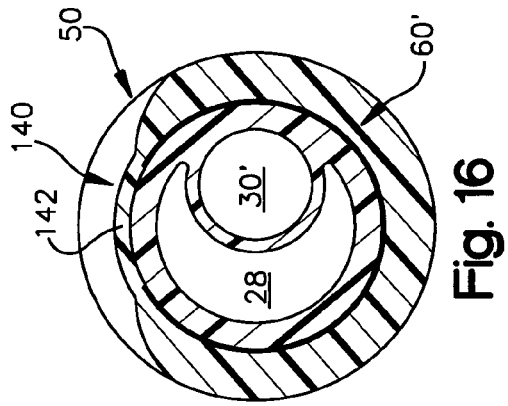

APPARATUS FOR AUTO-RETROPERFUSION OF A CORONARY VEIN

RELATED APPLICATION

This application is a continuation-in-part of application Ser. No. 10/786,788, filed on Feb. 25, 2004 now U.S. Pat. No. 7,004,925, which claims priority from U.S. provisional patent application Ser. No. 60/449,883, filed on Feb. 25, 2003. The subject matter of these earlier applications is incorporated herein by reference.

TECHNICAL FIELD

The present invention relates to an apparatus for automatically retroperfusing a coronary vein with oxygenated blood from an artery.

BACKGROUND OF THE INVENTION

In the United States alone, over 1.5 million persons annually suffer from intractable ischemia or acute myocardial infarction, or both. It is known to use retroperfusion techniques to treat such conditions. Retroperfusion techniques for the heart generally involve the delivery of arterial oxygenated or venous blood. This blood is delivered retrogradedly to the endangered ischemic myocardium through its adjoining coronary veins in a direction opposite to the normal outflow of venous blood through that vein. That retroperfused blood crosses from the coronary veins into the tissue capillary circulation, e.g., as microcirculation, to provide blood and nourishment to an underperfused myocardium.

Coronary sinus retroperfusion limits or reduces myocardial damage when administered as a preemptive or remedial treatment, or both. Coronary sinus retroperfusion also may be effective therapy when targeted to slow or, in some cases, reverse the progression from myocardial ischemia to the irreversible damage associated with myocardial infarction. Further, coronary sinus retroperfusion may provide a temporary therapeutic window to achieve even more complete revascularization, such as by Percutaneous Transluminal Coronary Angioplasty (PTCA) or Coronary Artery By-Pass Grafting (CABG), and may also permit physicians to improve myocardial salvage.

Typically, a two-step surgical procedure is utilized that involves creating an interventional shunt from an artery to the coronary sinus (venous circulation), and subsequently restricting the blood flow through the coronary sinus, such as with an occluding balloon, to facilitate effective retroperfusion of coronary veins with arterial blood provided via an intraluminal catheter. The occlusion of the coronary sinus helps to prevent excessive back-flow of blood into the right atrium.

The balloon used to occlude the coronary sinus is often also used to retain the intraluminal catheter in place inside the patient. The balloon is inflated inside the ostium downstream of the middle cardiac vein (serving the right ventricular territory), in the space between the middle cardiac vein and the veins coming from the left ventricle. This infusion thus occurs distal to the balloon. Because the space upstream of the middle cardiac vein between the ostium and the middle cardiac vein is too small to contain the balloon, the middle cardiac vein must be excluded from the perfusion. Consequently, the right ventricle is left unprotected during heart surgery. Therefore, although vessel occlusion may be required in a retroperfusion procedure, use of the inflated balloon to occlude the vessel can be disadvantageous.

Attempts have been made to improve the catheter design to minimize the obstruction of the branch lumens. These catheter designs included shortening the retention balloons. Although the use of protuberances or ridges on the balloon surface to improve the frictional contact has been suggested, the shortened balloon may provide insufficient frictional contact with the lumen surface. Fixation balloons made of an open-walled element material, which permits blood to flow freely through the open-walled element material, are also known.

SUMMARY OF THE INVENTION

The present invention provides an apparatus for automatically retroperfusing a coronary vein with oxygenated blood from an artery. The apparatus comprises an intraluminal cannula having a main body portion extending between a proximal end portion and a distal end portion. The proximal end portion is for connecting to an artery outside of the pericardium to automatically supply oxygenated blood from the artery for retroperfusion of the coronary vein. The main body portion and the distal end portion are insertable through a vein that is fluidly connected with the coronary vein to be retroperfused and into the coronary vein. An expandable stent is attached to the distal end portion of the cannula for expanding radially into engagement with the interior wall of the coronary vein to secure the distal end portion at a location within the coronary vein. Occluding means for at least partially occluding the coronary vein is provided to decrease the back-flow of blood into the right atrium during retroperfusion. The occluding means is located at the distal end portion of the cannula. The occluding means includes at least one valve portion that is positioned about the distal end portion of the cannula. The at least one valve portion allows a limited quantity of antegrade blood flow.

In accordance with another aspect of the invention, the at least one valve portion of the occluding means comprises an unattached flap that is selectively disengageable from the outer surface of the distal end of the cannula to define an annular opening through which a limited quantity of blood may flow.

In accordance with another aspect of the invention, the occluding means comprises an inflatable balloon. The inflatable balloon is attached substantially circumferentially about the distal end portion of the cannula except the at least one valve portion, which is formed by an unattached flap. The unattached flap defines an annular opening around the outer surface of the cannula through which a limited quantity of blood may flow.

In accordance with another aspect, the present invention provides an apparatus for automatically retroperfusing a coronary vein with oxygenated blood from an artery. The apparatus comprises an intraluminal cannula having a main body portion extending between a proximal end portion and a distal end portion. The proximal end portion is for connecting to an artery to automatically supply oxygenated blood from the artery for retroperfusion of the coronary vein. The main body portion and the distal end portion are insertable through a vein that is fluidly connected with the coronary vein to be retroperfused and into the coronary vein. An expandable stent is attached to the distal end portion of the cannula for expanding radially into engagement with the interior wall of the coronary vein to secure the distal end portion at a location within the coronary vein. Occluding means for at least partially occluding the coronary vein is provided to decrease the back-flow of blood into the right atrium during retroperfusion. The occluding means is disposed within the stent. The occluding means includes at least one valve portion that is positioned about the distal end portion of the cannula. The at least one valve portion allows a limited quantity of antegrade blood flow.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 1 is a side view, partly in section, of an apparatus for automatically retroperfusing a coronary vein in accordance with a first embodiment of the present invention, the apparatus being shown in a first condition;

FIG. 2 is a view similar to FIG. 1 illustrating the apparatus in a second condition;

FIG. 2A is an enlarged view of an end portion of the apparatus shown in FIG. 2;

FIG. 3 is a section view taken along line 3-3 in FIG. 2A;

FIG. 9 is a side view, partly in section, of an apparatus for automatically retroperfusing a coronary vein in accordance with a second embodiment of the present invention, the apparatus being shown in a first condition;

FIG. 10 is a section view of an end portion of the apparatus of FIG. 9 illustrating the apparatus in a second condition;

FIG. 11 is a section view taken along line 11-11 in FIG. 10;

FIG. 15 is a section view of an end portion of an apparatus for automatically retroperfusing a coronary vein in accordance with a fourth embodiment of the present invention, the apparatus being shown in a second condition;

FIG. 16 is a section view taken along line A-A in FIG. 15;

FIG. 16A is a section view taken along line A-A in FIG. 15 with valve portion open;

DESCRIPTION OF EMBODIMENTS

Figure 4:
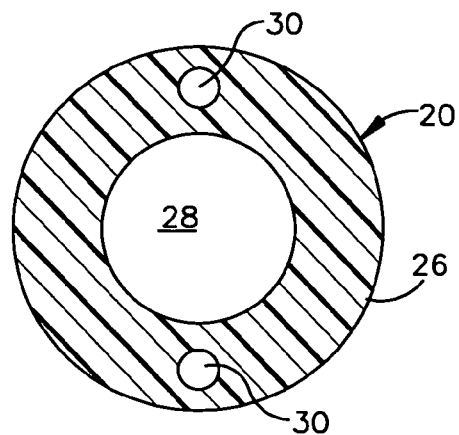
FIG. 4 is a section view taken along 4-4 in FIG. 3.

The present invention relates to an apparatus and method for automatically retroperfusing a coronary vein with oxygenated blood from an artery to treat severely symptomatic patients requiring an increase of oxygen supply to an ischemic myocardium. As representative of the present invention, FIG. 1 illustrates an apparatus 10 for automatically retroperfusing a coronary vein in accordance with a first embodiment.

The apparatus 10 includes an intraluminal cannula 20. The cannula 20 has a main body portion 22 that extends between a proximal end portion 24 and a distal end portion 26. The main body portion 22 is constructed from a biocompatible, non-thrombogenic material including but not limited to PTFE, silicon rubber, or polyurethane. The main body portion 22 could alternatively be made from a biological material.

As best seen in FIGS. 3 and 4, the main body portion 22 of the cannula 20 has a centrally located primary lumen 28 and a pair of oppositely disposed secondary lumens 30. It should be understood, however, that the cannula 20 could have more than the three lumens 28 and 30, and could have a variety of different configurations for the lumens in the cannula. The primary lumen 28 is larger in diameter than the secondary lumens 30 and is the passage through which oxygenated blood will flow. Accordingly, it is contemplated that the blood-contacting interior surface 32 of the primary lumen 28 may be exposed material or may act as a matrix for cell in-growth from host or seeded culture cells.

The proximal end portion 24 of the cannula 20 includes a pair of proximal extensions 34 (FIG. 1) that branch from the cannula and a graft section 36 for suturing to an artery outside of the pericardium to automatically supply oxygenated blood from the artery for retroperfusion of the coronary vein. The graft section 36 is a flexible tubular member that is fluidly connected to the primary lumen in the cannula. The graft section 36 is constructed from a suitable suturable material including but not limited to expanded PTFE, polyurethane, or a synthetic fabric such as Dacron®. The graft section 36 could alternatively be made from a biological tissue.

Each of the proximal extensions 34 at the proximal end portion 24 of the cannula 20 is fluidly connected, in a manner not shown, to a respective one of the secondary lumens 30 in the main body portion 22 of the cannula. Further, each of the proximal extensions 34 includes an end section that functions as a subcutaneous access port 38.

At the distal end portion 26 of the cannula 20, the primary lumen 28 terminates in an axial opening 40 at the terminal end of the cannula as shown in FIG. 3. Each of the two secondary lumens 30 terminates in a radial aperture 42 that is located adjacent the terminal end.

A radially expandable stent 50 is attached to the distal end portion 26 of the cannula 20. The stent 50 may be made of a variety of expandable materials including but not limited to polymeric materials, stainless steel, a NiTi alloy, a pseudoelastic NiTi alloy having a phase transition temperature above body temperature, cobalt, nickel, molybdenum, and a chromium alloy such as MP35N.

The stent 50 is disposed circumferentially about the distal end portion 26 of the cannula 20 and has oppositely disposed first and second ends 52 and 54. The first end 52 of the stent 50 is positioned nearest the terminal end of the cannula 20. The first end 52 is not attached to the cannula 20 and is radially expandable from a collapsed condition shown in FIG. 1 to an expanded condition shown in FIG. 2. The second end 54 of the stent 50 is secured to the outside of the distal end portion 26 of the cannula 20. The second end 54 may be secured to the cannula 20 by a collar 56 or any other suitable means.

The apparatus 10 further includes a membrane 60 for at least partially occluding the coronary vein to decrease the back-flow of blood into the right atrium during retroperfusion. The membrane 60 is located at the distal end portion 26 of the cannula 20 within the stent 50. The membrane 60 may be made from a biocompatible, non-thrombogenic synthetic material or a biological material. The surfaces of the membrane 60 may also be seeded with host or cultured cells to act as a matrix for cell in-growth.

The membrane 60 has an umbrella shape defined by an open end 62 and a closed end 64. The closed end 64 is attached to the outer surface of the distal end portion 26 of the cannula 20. The collar 56 used to secure the second end 54 of the stent 50 to the cannula 20 may also serve to secure the closed end 64 of the membrane 60 to the cannula. The open end 62 of the membrane 60 is attached to the stent 50 by sutures 66 (FIG. 3) or another suitable means so that, when the stent is expanded, the membrane spans the radial distance between the interior of the stent and the outer surface of the cannula 20 as shown in FIGS. 2 and 3. The membrane 60 includes one or more openings 68 to allow limited blood flow through the membrane in order to decrease the back-flow of blood into the right atrium during retroperfusion.

The apparatus 10 further includes a removable sheath 70 (FIG. 1) that encloses the main body portion 22 and the distal end portion 26 of the cannula 20 and constrains the stent 50 in the collapsed condition of FIG. 1. As may be seen in FIGS. 2, 2A, and 3, when the sheath 70 is pulled toward the proximal end portion 24 of the cannula 20 in the direction of arrow A in FIG. 2, the stent 50 and the open end 62 of the membrane 60 attached thereto expand to their respective expanded conditions. The sheath 70 may also include a predetermined axial tear line (not shown) to permit the sheath to be peeled off the cannula 20 as the sheath is pulled proximally.

Figure 5:
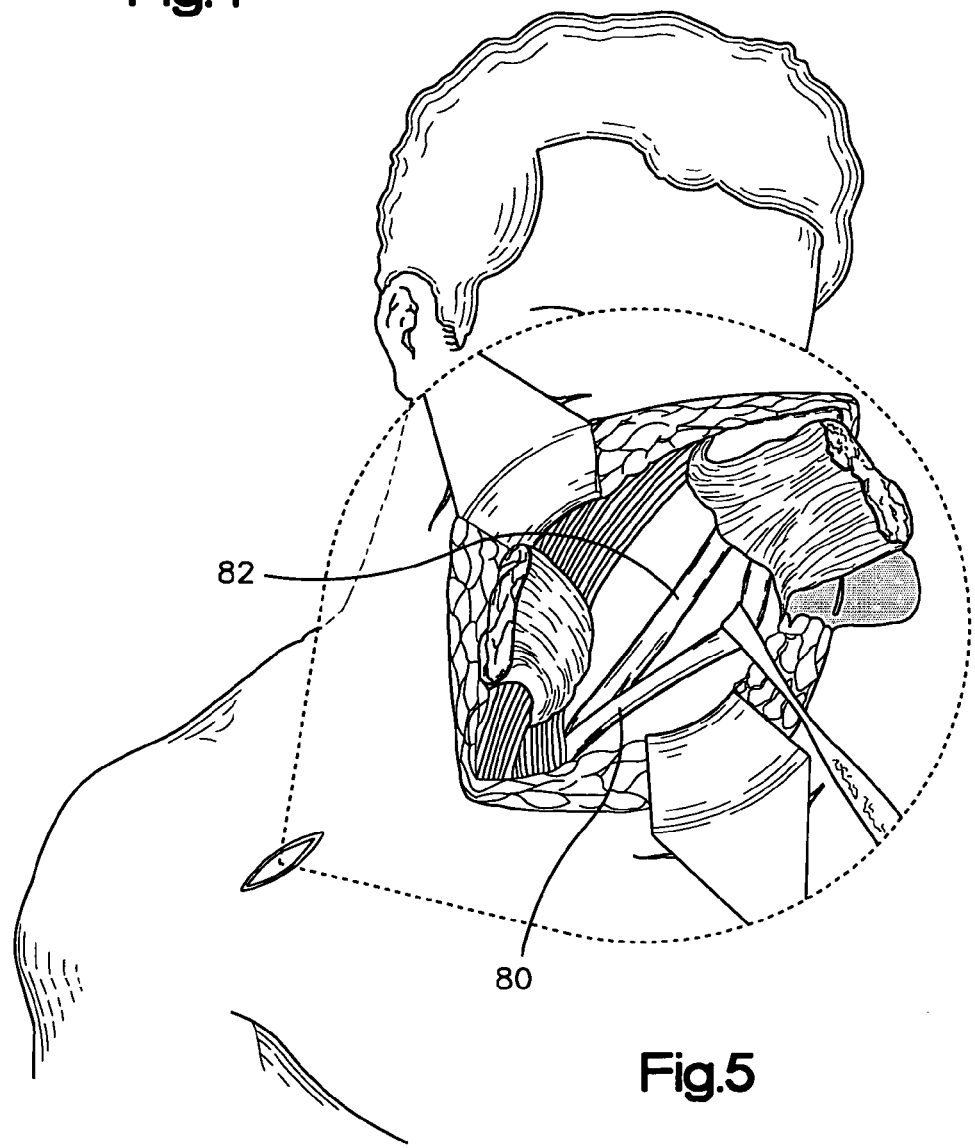
FIG. 5 is a front view of a patient and includes an enlarged area illustrating the location where the apparatus is inserted into the patient.

To perform automatic retroperfusion using the apparatus 10 in accordance with one embodiment of the present invention, the axillary vein 80 and the axillary artery 82 are exposed as shown in FIG. 5. The distal end portion 26 of the cannula 20 is then introduced into the axillary vein 80 using the known Seldinger technique, which includes passing the cannula over a guidewire 84, under direct vision. During this step, the primary lumen 28 of the cannula 20 is used by the guidewire 84. The distal end portion 26 of the cannula 20 is then directed, via fluoroscopy, direct vision, transesophageal echiocardiogram, or other suitable means, through the vasculature (i.e., the subclavian vein and the superior vena cava) and into the right atrium of the heart. The distal end portion 26 of the cannula 20 is further advanced through the right atrium and into the coronary sinus 86, which is the coronary vein to be retroperfused.

Figure 6:
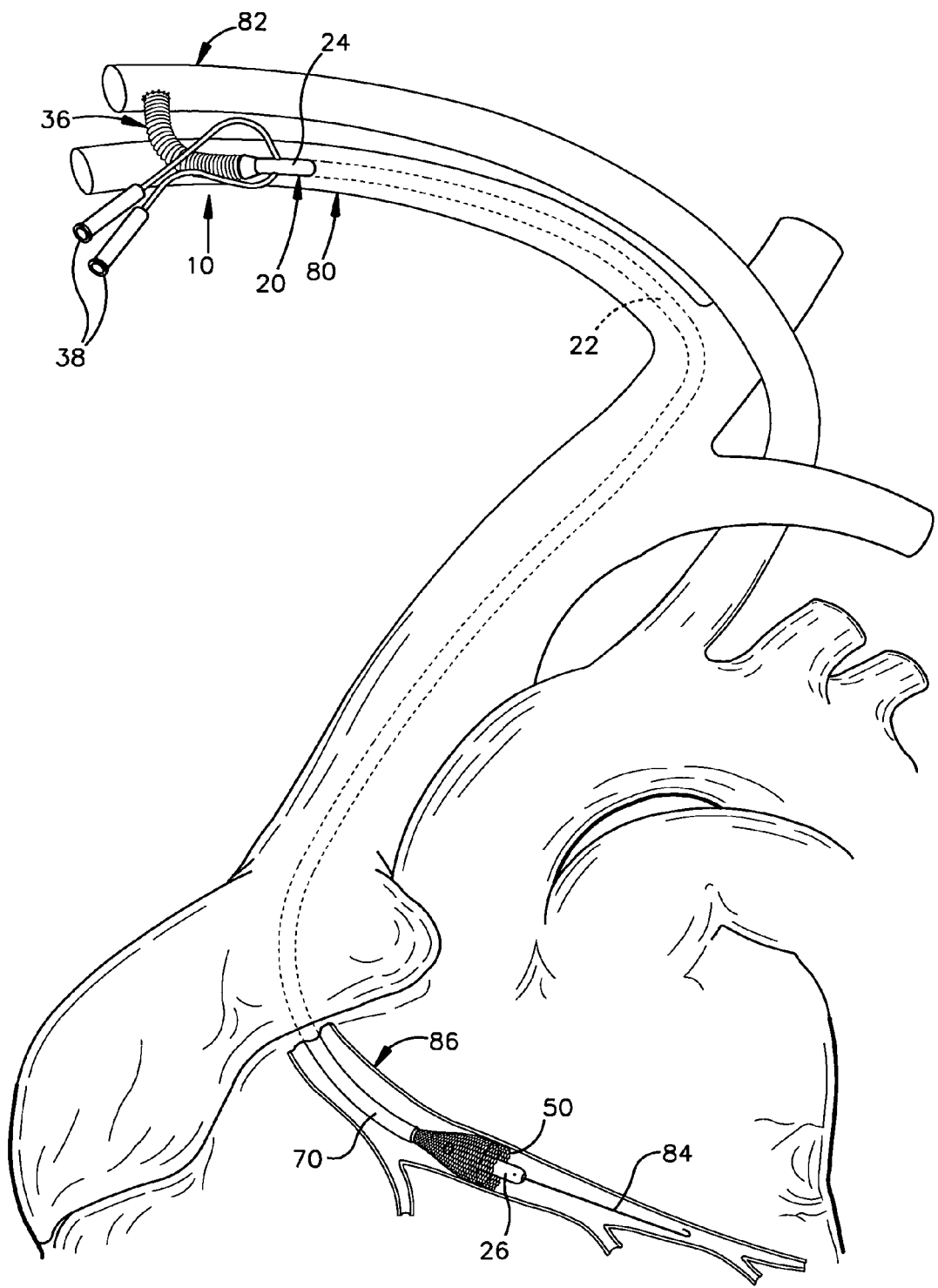
FIG. 6 is a schematic view of the apparatus being passed through a vein and the right atrium to a location in a coronary vein to be retroperfused.
Figure 7:
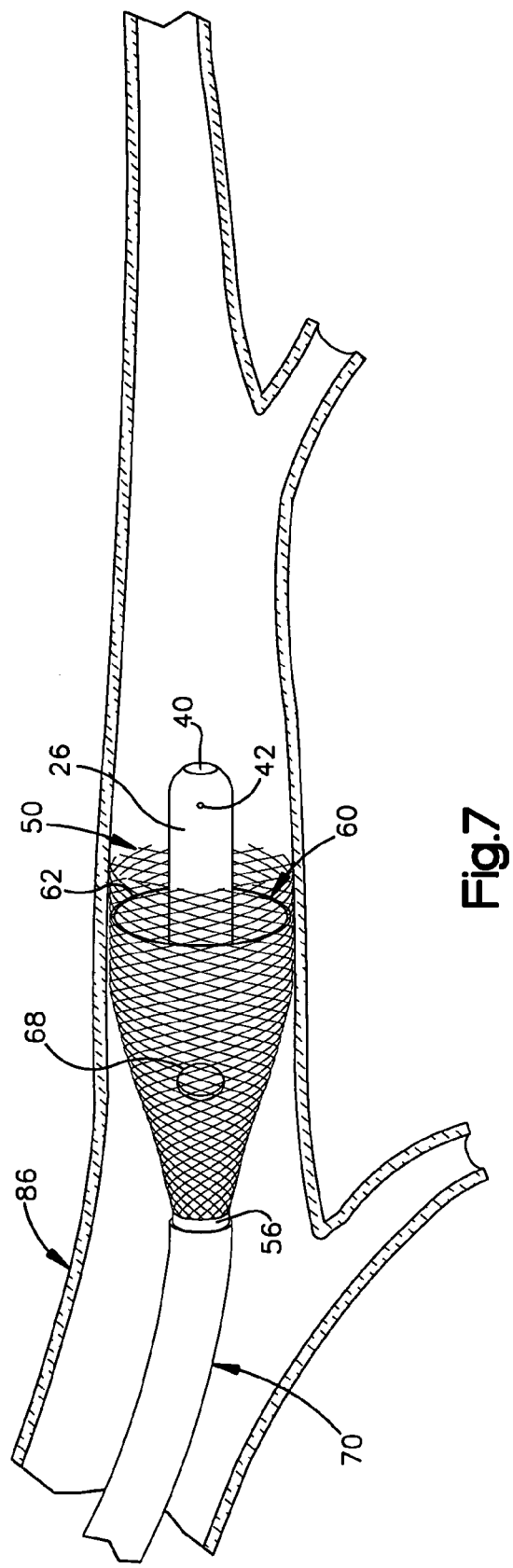
FIG. 7 is an enlarged view of a portion of FIG. 6 illustrating an end portion of the apparatus in the coronary vein.

When the distal end portion 26 of the cannula 20 reaches the desired location in the coronary sinus 86, the sheath 70 is pulled proximally to release the stent 50 for expansion. The stent 50 then expands radially into engagement with the walls of the coronary sinus 86 to secure the distal end portion 26 of the cannula 20 in the coronary sinus 86 as shown in FIGS. 6 and 7. As the stent 50 expands into engagement with the interior wall of the coronary sinus 86, the open end 62 of the membrane 60 is stretched across the coronary sinus 86 and spans the radial distance between the interior wall of the coronary sinus and the outer surface of the cannula 20. As may be seen in FIG. 7, with the distal end portion 26 of the cannula 20 secured in the coronary sinus 86 by the stent 50, the guidewire 84 is then removed. The sheath 70 is also removed from the cannula 20.

Next, an anastomosis of the proximal end portion 24 of the cannula 26 and the axillary artery 82 is accomplished by suturing the graft section 36 to the axillary artery as shown in FIG. 6. Normal antegrade blood flow continues as usual, but oxygenated blood is now automatically retroperfused through the cannula 20 to the ischemic myocardium via the coronary sinus 86. The oxygenated blood flow through the cannula 20 occurs throughout the cardiac cycle with a pulsatile flow pattern, but with a peak flow and pressure at the end of systole and the beginning of diastole. Excessive back-flow of blood into the right atrium from the coronary sinus 86 is prevented by the membrane 60.

It should be noted that the aforementioned procedure can be done under local anesthesia. Depending on the patient's particular condition, auto-retroperfusion can last for minutes, hours, days, or months. During retroperfusion, the secondary lumens 30 can be used for coronary sinus pressure measurement and the delivery of drugs, cells, genes, or growth factors. In accordance with the first embodiment of FIGS. 1-7, it is expected that the access ports 38, which are fluidly connected with the secondary lumens 30, and the graft section 36 will be subcutaneous.

Figure 8:
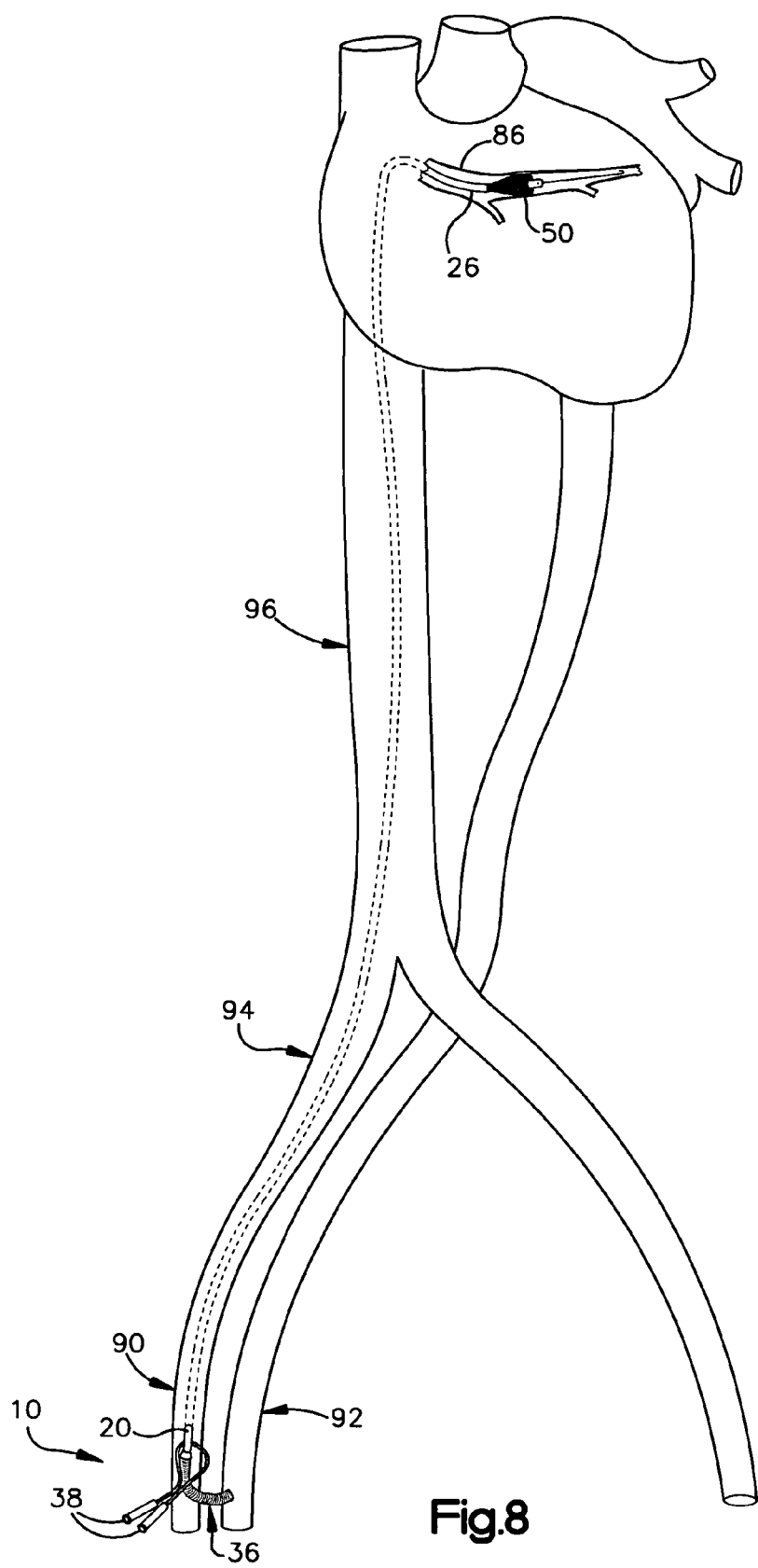
FIG. 8 is a schematic view of the apparatus of FIG. 1 being passed through a different vein to the location in a coronary vein to be retroperfused and also illustrates a different artery for providing the oxygenated blood.
Figure 12:
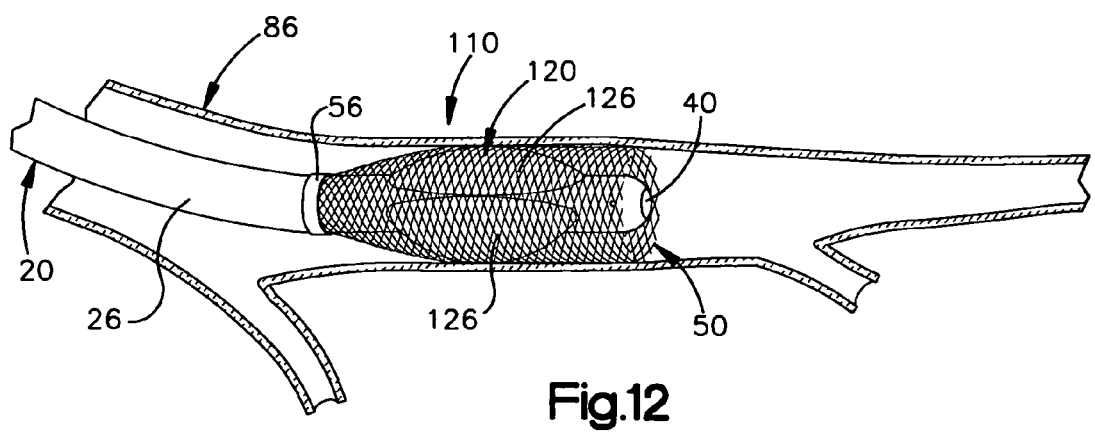
FIG. 12 is a schematic view of the apparatus of FIG. 9 illustrating the end portion in the coronary vein.

FIG. 8 illustrates use of the apparatus 10 to automatically retroperfuse the coronary sinus 86 though an anastomosis between the femoral vein 90 and the femoral artery 92. The distal end portion 26 of the cannula 20 is passed through the femoral vein 90, the iliac vein 94, and the inferior vena cava 96 to the right atrium of the heart. The distal end portion 26 of the cannula 20 is then advanced into the coronary sinus 86 and secured by the stent 50 in the same manner as discussed above. Finally, the graft section 36 at the proximal end 26 of the cannula 20 is sutured to the femoral artery 92 to provide oxygenated blood for retroperfusion of the coronary sinus 86. As with the previous embodiment, the entire apparatus 10, including the graft section 36 and the ports 38, remain subcutaneous following the anastomosis.

FIGS. 9-12 illustrate an apparatus 110 for automatically retroperfusing a coronary vein in accordance with a second embodiment of the present invention. In the second embodiment of FIGS. 9-12, reference numbers that are the same as those used in the first embodiment of FIGS. 1-7 designate parts that are the same as parts in the first embodiment. The apparatus 110 according to the second embodiment is similar to the apparatus 10 of the first embodiment, but does not include the membrane 60. Rather, according to the second embodiment of the present invention, the means for at least partially occluding the coronary sinus 86 is an inflatable balloon 120.

The balloon 120 is attached to the distal end portion 26 of the cannula 20 within the stent 50. The balloon 120 is inflatable from a collapsed condition shown in FIG. 9 to an inflated condition shown in FIGS. 10-12. The balloon 120 may be made from a biocompatible, non-thrombogenic synthetic material or a biological material. The outer surfaces of the balloon 120 may be seeded with host or cultured cells to act as a matrix for cell in-growth.

The balloon 120 has oppositely disposed first and second axial ends 122 and 124 (FIG. 10) and a plurality of lobes 126 that extend circumferentially about the distal end portion 26 of the cannula 20 between the first and second ends of the balloon. The lobes 126 define a plurality of radial gaps 128 between the lobes that allow a limited amount of blood flow past the balloon 120. As may be seen in FIG. 11, a plurality of tertiary lumens 130 may be present in the cannula 20 and fluidly connected with the lobes 126 of the balloon 120 so that the lobes can be inflated via one or more additional subcutaneous (or percutaneous) access ports (not shown). It is contemplated that the lobes 126 could also be self-inflated by blood during systole, which would advantageously allow the flow restriction to increase or decrease with a corresponding increase or decrease in coronary sinus pressure.

Automatic retroperfusion using the apparatus 110 according to the second embodiment of FIGS. 9-12 is nearly identical to the method discussed above with regard to the first embodiment of FIGS. 1-7, with the exception that the lobes 126 of the balloon 120 are inflated to at least partially occlude the coronary sinus 86 rather than the membrane 60 performing this function. As with the first embodiment, after the anastomosis of the graft section 36 at the proximal end portion 24 of the cannula 20 and the axillary artery 82 is completed, oxygenated blood is automatically retroperfused through the cannula to the ischemic myocardium via the coronary sinus 86. The oxygenated blood flow through the cannula 20 occurs throughout the cardiac cycle with a peak flow and pressure at the end of systole and the beginning of diastole, and with excessive back-flow of blood into the right atrium from the coronary sinus 86 being prevented by the balloon 120.

Figure 13:
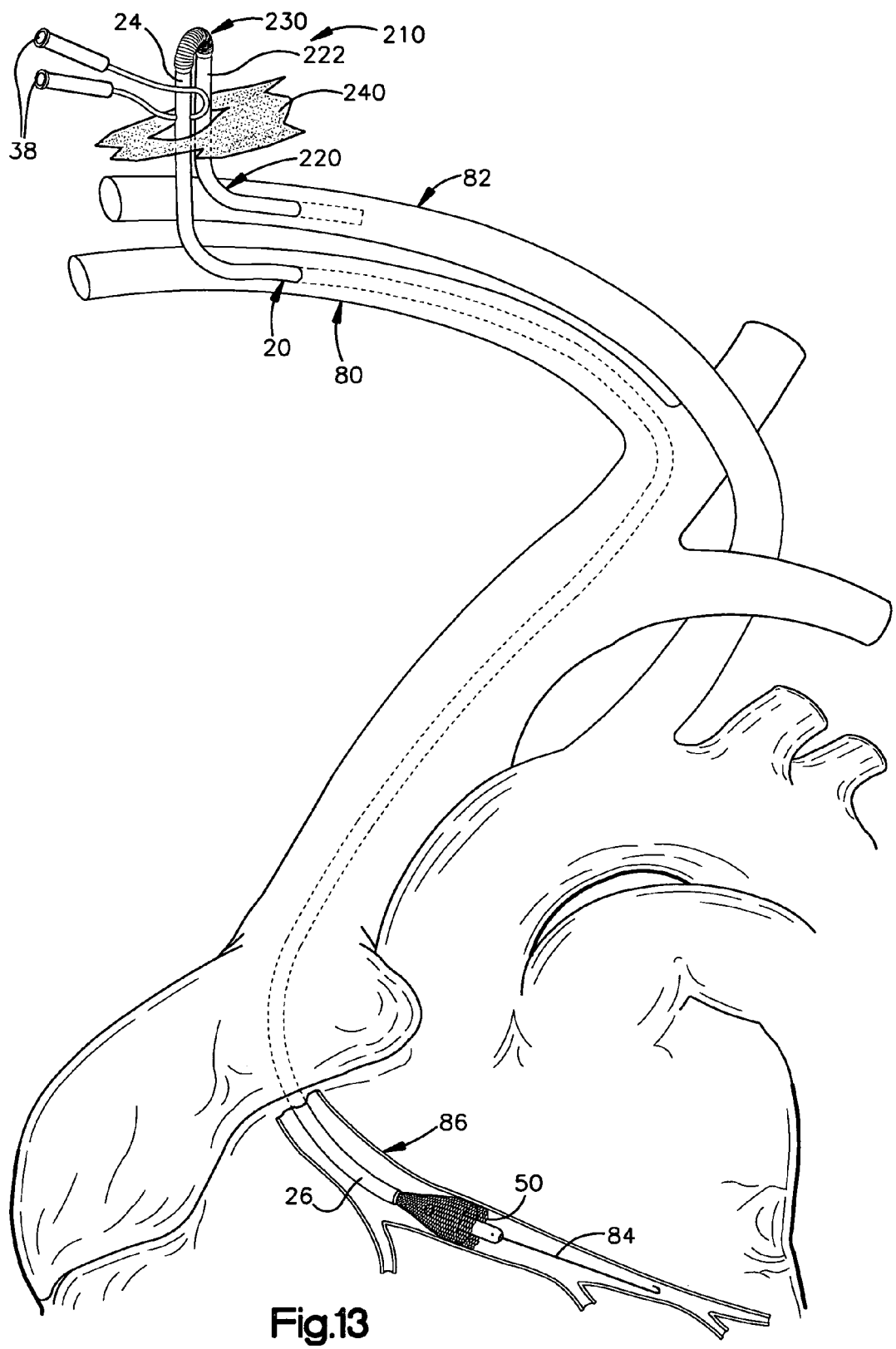
FIG. 13 is a schematic view of an apparatus for automatically retroperfusing a coronary vein in accordance with a third embodiment of the present invention, the apparatus being shown in an installed condition.

FIG. 13 illustrates an apparatus 210 for automatically retroperfusing a coronary vein in accordance with a third embodiment of the present invention. In the third embodiment of FIG. 13, reference numbers that are the same as those used in the first embodiment of FIGS. 1-7 designate parts that are the same as parts in the first embodiment.

The apparatus 210 according to the third embodiment is similar to the apparatus 10 of the first embodiment, but without the graft section 36 at the proximal end portion 24 of the cannula 20. Instead, the apparatus 210 includes a separate percutaneous catheter 220 for accessing the axillary artery 82 and a connecting tube 230 for fluidly coupling the catheter with the proximal end portion 24 of the cannula 20. As may be seen in FIG. 13, a proximal end 222 of the catheter 220, the proximal end portion 24 of the cannula 20 including the access ports 38, and the connecting tube 230 all lie above the skin 240 during the retroperfusion process.

Automatic retroperfusion using the apparatus 210 according to the third embodiment of FIG. 13 is nearly identical to the method discussed above with regard to the first embodiment of FIGS. 1-7, with the exception that, following insertion of the cannula 20 into the axillary vein 80 and subsequent advancement into the coronary sinus 86, the catheter 220 is inserted into the axillary artery 82. The connecting tube 230 is then attached between the proximal end portion 24 of the cannula 20 and the catheter 220 to supply oxygenated blood for automatic retroperfusion through the cannula to the ischemic myocardium via the coronary sinus 86. It should be noted that either the membrane 60 shown in FIG. 13 or the previously described balloon 120 can be used to prevent excessive back-flow of blood into the right atrium from the coronary sinus 86.

Figure 14:
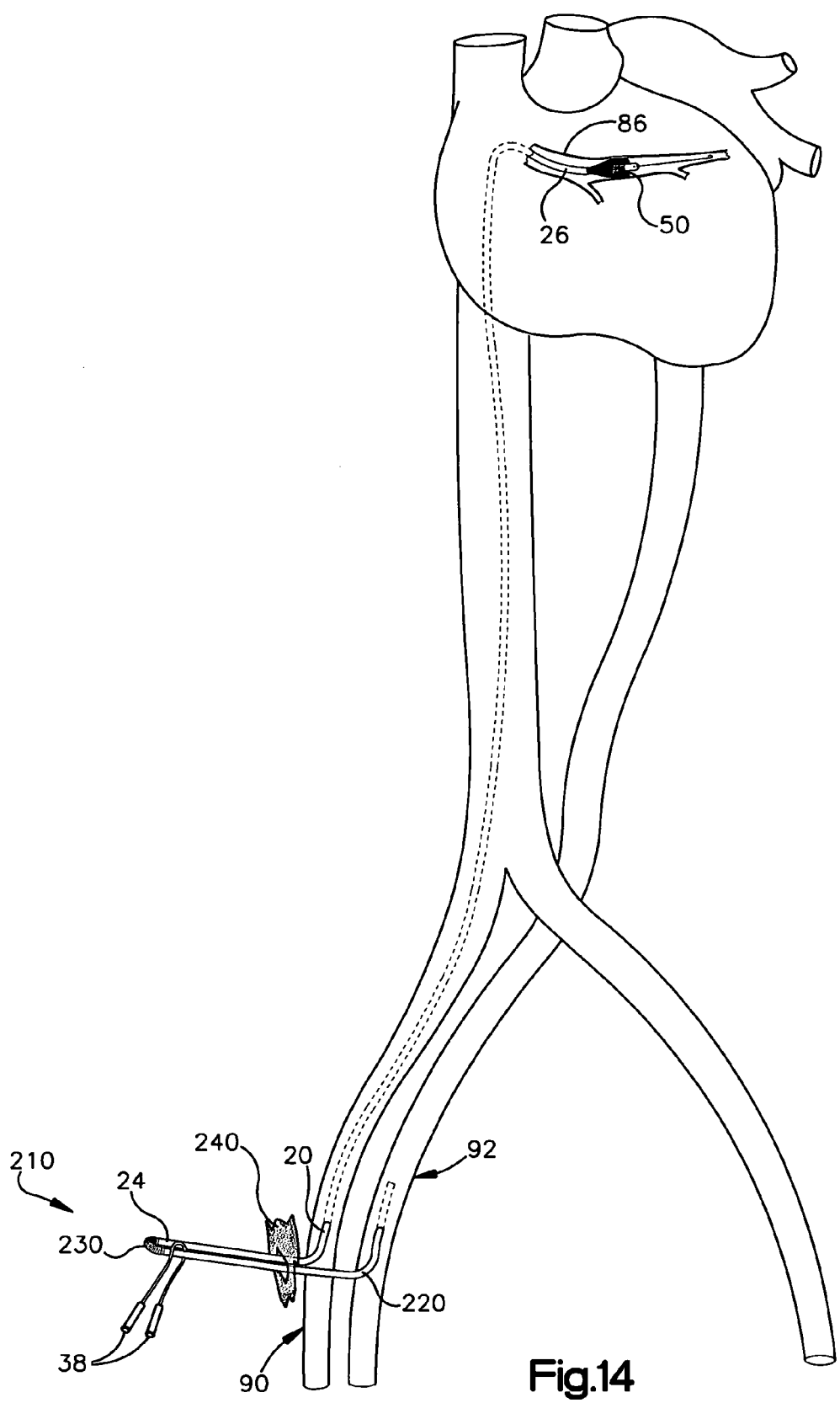
FIG. 14 is a schematic view of the apparatus of FIG. 13 being passed through a different vein to the location in a coronary vein to be retroperfused and also illustrates a different artery for providing the oxygenated blood.

FIG. 14 illustrates use of the apparatus 310 to automatically retroperfuse the coronary sinus 86 via a fluid connection between the femoral vein 90 and the femoral artery 92. Following insertion of the cannula 20 into the femoral vein 90 and subsequent advancement into the coronary sinus 86, the catheter 220 is inserted into the femoral artery 92 and the connecting tube 230 is attached between the catheter and the proximal end portion 24 of the cannula 20. As may be seen in FIG. 14, the proximal end 222 of the catheter 220, the proximal end portion 24 of the cannula 20 including the access ports 38, and the connecting tube 230 all lie above the skin during the retroperfusion process.

FIGS. 15-16A illustrate an apparatus 310 for automatically retroperfusing a coronary vein in accordance with a fourth embodiment of the present invention. In the fourth embodiment of FIGS. 15-16, reference numbers that are the same as those in the first embodiment of FIGS. 1-7 designate parts that are the same as parts in the first embodiment. The apparatus 310 according to the fourth embodiment is similar to the apparatus 10 of the first embodiment, but uses a membrane 60' that does not include one or more openings 68 to allow limited blood flow through the membrane in order to decrease the back-flow of blood into the right atrium during retroperfusion. Membrane 60' is otherwise identical to membrane 60. Rather, according to the fourth embodiment of the present invention, the means for allowing limited antegrade blood flow is at least one valve portion 140 defined by the attachment of membrane 60' to the distal end portion 26 of the cannula 20.

The membrane 60' has an umbrella shaped defined by an open end 62 and a closed end 64. The closed end 64 is substantially circumferentially attached to the outer surface of the distal end portion 26 of the cannula 20 except that at least one flap 142 of the closed end 64 is unattached. The valve portion 140 is formed by the unattached flap 142, and is selectively disengageable from the outer surface of the distal end portion 26 of the cannula 20. Once the stent 50 is expanded, the valve portion 140 is allowed to expand away from the outer surface of the distal end portion 26 of cannula 20 as the venous pressure increases. This expansion creates an annular opening 144 through which a limited quantity of blood may flow. A depiction of the valve portion 140 in this expanded state is shown in FIG. 16A.

Apparatus 310 further comprises a secondary lumen 30' that can be used for coronary sinus pressure measurement and the delivery of drugs, cells, genes, or growth factors. Secondary lumen 30' is identical to secondary lumen 30 except for its profile in relation to primary lumen 28.

Figure 17:
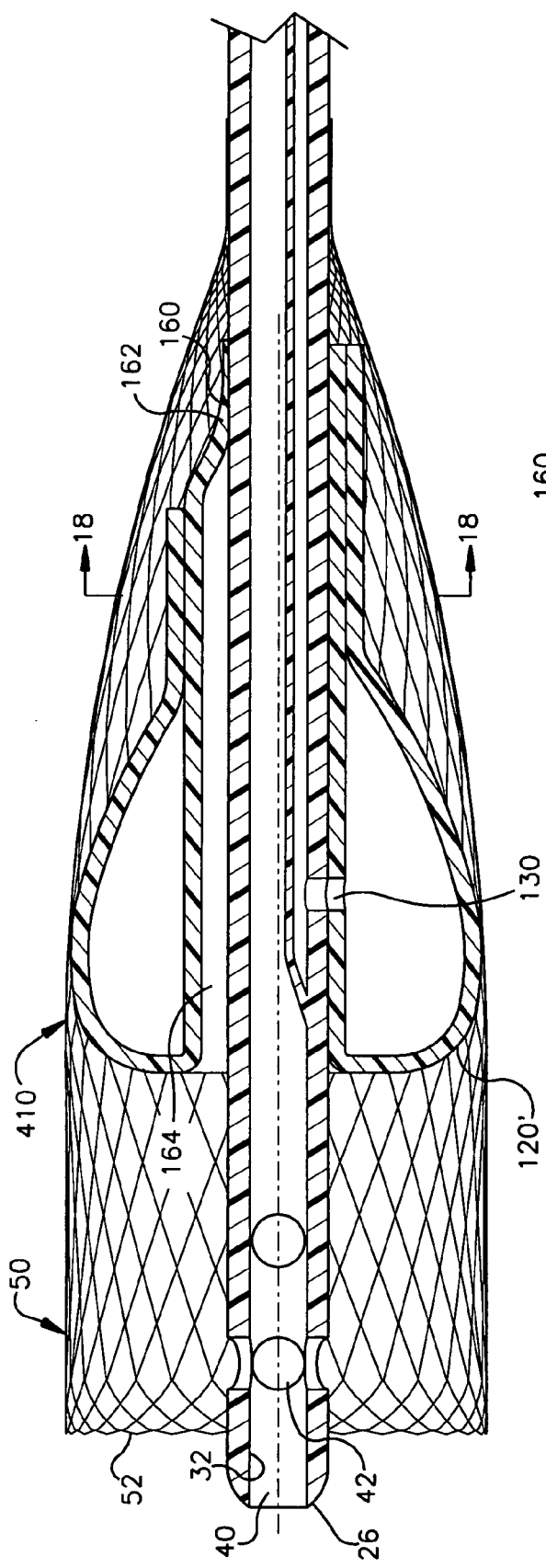
FIG. 17 is a section view of an end portion of an apparatus for automatically retroperfusing a coronary vein in accordance with a fifth embodiment of the present invention, the apparatus being shown in a second condition.
Figure 18:
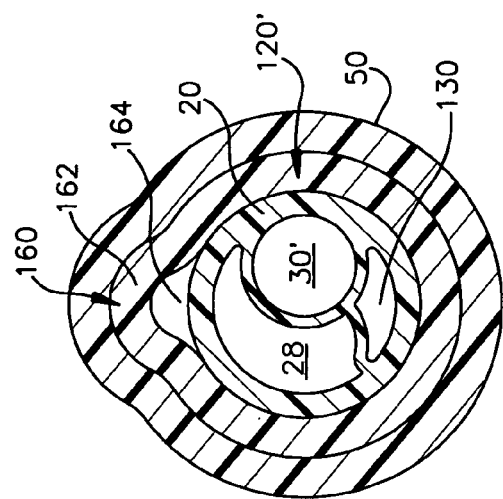
FIG. 18 is a section view taken along line A-A in FIG. 17.

FIGS. 17-18 illustrate an apparatus 410 for automatically retroperfusing a coronary vein in accordance with a fifth embodiment of the present invention. In the fifth embodiment of FIGS. 17-18, reference numbers that are the same as those in the first embodiment of FIGS. 1-7 designate parts that are the same as parts in the first embodiment. The apparatus 410 according to the fifth embodiment is similar to the apparatus 110 of the second embodiment, but uses a balloon 120' that does not include a plurality of lobes 126 that define a plurality of radial gaps 128 between the lobes that allow a limited amount of blood flow past the balloon 120. Balloon 120' is otherwise identical to balloon 120. Rather, according to the fifth embodiment of the present invention, the means for allowing limited antegrade blood flow is at least one valve portion 160 defined by the attachment of balloon 120' to the distal end portion 26 of the cannula 20.

The balloon 120' is attached substantially circumferentially about the distal end portion 26 of the cannula 20, except that there is at least one unattached flap 162 which forms the valve portion 160. The unattached flap 162 defines an annular opening 164 around the outer surface of the distal end 26 of the cannula 20 through which a limited quantity of blood may flow.

Apparatus 410 further comprises a secondary lumen 30' that can be used for coronary sinus pressure measurement and the delivery of drugs, cells, genes, or growth factors. Secondary lumen 30' is identical to secondary lumen 30 except for its profile in relation to primary lumen 28.

As mentioned previously, the apparatus of the present invention are aimed at treating severely symptomatic patients requiring an increase of oxygen supply to the ischemic myocardium. The indications known at the present time for implantation of the apparatus disclosed herein can be transient or definitive according to a patient's evolution as follows:

1. Stunned left ventricle (LV) or hybernating LV: EF<25%, with or without angina, with or without CHF symptoms with areas of myocardial viability;
2. AMI (with large ischemic area at risk with CHF symptoms) patients with more than 8 to 12 hs of evolution, with contraindications for fibrinolytic therapy and impossibility to perform rescue PTCA;
3. AMI with failed rescue PTCA, "No reflow phenomenon" (20-30% rescue AMI PTCA);
4. AMI—cardiogenic shock;
5. CHF FC III-IV with severe LV dysfunction (ischemic cardiomyopathy in heart transplant waiting list) or no option for heart transplant;
6. Severe stable or unstable angina in patients with severe diffuse coronary artery disease ("no option" patients for CABG or PTCA, 20 to 30% of the total coronary patients);
7. Redo coronary artery operation in patients, or "no option" patients indicated for CABG or PTCA;
8. Heart transplanted patients with progressive coronary artery disease;
9. High risk patients with concomitant diseases (COPD, chronic renal failure, neurological sequelae due to previous CVA with angina FC IV);
10. Drug delivery system: cardiotonics drugs, fibrinolytics, scavengers, blocking apoptosis, angiogenesis, myocites, etc.;
11. Improve or accelerate the Bridge to Recovery in LVAD patients; and
12. Chronic support as a destination therapy.

From the above description of the invention, those skilled in the art will perceive improvements, changes and modifications. For example, it is contemplated that the apparatus could be used in other suitable veins and/or arteries besides the axillary and femoral locations described above. Such improvements, changes and modifications within the skill of the art are intended to be covered by the appended claims.

Having described the invention, we claim:

1. An apparatus for automatically retroperfusing a coronary vein with oxygenated blood from an artery, said apparatus comprising:
   an intraluminal cannula having a main body portion extending between a proximal end portion and a distal end portion;
   said proximal end being configured to connect to an artery outside of the pericardium to automatically supply oxygenated blood from the artery for retroperfusion of the coronary vein;
   said main body portion and said distal end portion being insertable through a vein that is fluidly connected with the coronary vein to be retroperfused and into the coronary vein;
   an expandable stent attached to said distal end portion of said cannula for expanding radially into engagement with interior wall of the coronary vein to secure the distal end portion at a location within the coronary vein;
   occluding means for at least partially occluding the coronary vein to decrease the back-flow of blood into the right atrium during retroperfusion; said occluding means being located at said distal end portion of said cannula; and
   said occluding means including at least one valve portion positioned about said distal end portion of said cannula, said at least one valve portion allowing a limited quantity of antegrade blood flow;
   wherein said occluding means comprises an inflatable balloon, said balloon being attached substantially circumferentially about said distal end portion of said cannula except for said at least one valve portion which is formed by an unattached flap, said unattached flap defining an annular opening around an outer surface of said cannula through which a limited quantity of blood may flow.

2. An apparatus for retroperfusing a coronary vein with oxygenated blood from an artery, said apparatus comprising:
   an intraluminal cannula having a main body portion extending between a proximal end portion and a distal end portion, said proximal end portion being configured to connect to a source for oxygenated blood;
   said main body portion and said distal end portion being insertable through a vein that is fluidly connected with the coronary vein to be retroperfused and into the coronary vein;
   an expandable stent attached to said distal end portion of said cannula for expanding radially into engagement with the interior wall of the coronary vein to secure the distal end portion at a location within the coronary vein; and
   occluding means for at least partially occluding the coronary vein to decrease the back-flow of blood into the right atrium during retroperfusion; said occluding means being located at said distal end portion of said cannula; and
   said occluding means including at least one valve portion positioned about said distal end portion of said cannula, said at least one valve portion allowing a limited quantity of antegrade blood flow;
   wherein said occluding means comprises an inflatable balloon, said balloon being attached substantially circumferentially about said distal end portion of said cannula except for said at least one valve portion which is formed by an unattached flap, said unattached flap defining an annular opening around an outer surface of said cannula through which a limited quantity of blood may flow.

* * * * *